United States Patent [19]

Pettit et al.

[11] Patent Number: 5,583,224
[45] Date of Patent: Dec. 10, 1996

[54] ISOLATION AND ELUCIDATION OF CEPHALOSTATIN 7, 8 AND 9

[75] Inventors: George R. Pettit, Paradise Valley, Ariz.; Yoshiaki Kamano, Tokyo, Japan

[73] Assignee: Arizona Board of Regents acting on behalf of Arizona State University, Tempe, Ariz.

[21] Appl. No.: 6,371

[22] Filed: Jan. 19, 1993

[51] Int. Cl.$^6$ .................... C07D 241/00; A61K 31/495
[52] U.S. Cl. ............................. 544/230; 514/249
[58] Field of Search .................... 544/338, 230; 514/249

[56] References Cited

PUBLICATIONS

Pettit, G. R. et al 'Antineoplastic Agents. 214. Isolation and Structure of Cephalostatins 7–9' J. Org. Chem (1992), 57(2), 429–431.

Primary Examiner—C. Warren Ivy
Assistant Examiner—Amelia Owens
Attorney, Agent, or Firm—Richard R. Mybeck; Walter R. Mybeck, II

[57] ABSTRACT

Substantially pure compositions of matter selected from the group of cephalostatin 7, cephalostatin 8, and cephalostatin 9 having anti-neoplastic activity are disclosed.

4 Claims, No Drawings

ISOLATION AND ELUCIDATION OF CEPHALOSTATIN 7, 8 AND 9

The work described herein was partially funded by grants under OIG grant CA 44344-01A1 awarded by the NCI and numerous private foundations. The United States Government may have certain rights to this invention.

INTRODUCTION

The present invention relates to the isolation and structural elucidation of new substances of marine origin herein denominated "Cephalostatin 7, 8 and 9". These Cephalostatins have been found to be powerful inhibitors of various human tumor cell lines.

BACKGROUND OF THE INVENTION

The invertebrate chordates have some vertebrate characteristics such as a dorsal tubular nervous system and notochord. Among such phyla lacking a vertebral column occurs the Hemichordata. The class Pterobranchia of this phylum has not previously been explored with respect to biologically active or other chemical constituents.

In late 1972, the Cancer Research Institute, Tempe, Ariz., collected by SCUBA (ca. 20 m) in the Indian Ocean off Southeast Africa, in areas patrolled by the great white shark *Carchorodon carchoris,* specimens from this class of the marine worm (approx. 5 mm long in tube colonies) *Cephalodiscus gilchristi* (order *cephalodiscida*). Two years later, methanol and water extracts of *C. gilchristi* demonstrated a confirmed active level against the U.S. National Cancer Institute's murine P388 lymphocytic leukemia (PS system) and obtained a 32–41% life extension at 25–37.5 mg/kg. After almost twenty years of relentless research directed at discovering the active constituent(s) of *C. gilchristi,* the isolation and structural elucidation of several of these new and powerful cell growth inhibitory substances with PS cell line $ED_{50}$ of $10^{-7}$ to $10^{-9}$ µg/mL has occurred.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data approaches ten million dollars per compound. As such, economics dictate that such a huge investment will be made only when there is a reasonable likelihood for it to be recovered. Absent such likelihood, there will be no investment and the research involving the discovery of these potentially life saving compounds will cease. Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and has been accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, Oct. 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports*, Vol. 81, No. 14, Page 1088, Jul. 14, 1989 for a description of the methods of statistical analysis. Both of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The impairment of human cancerous tumor growth is utilitarian in that it relieves these conditions, thereby allowing the human thus affected to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive for further research.

The recognition of antineoplastic and tumor inhibiting activity as demonstrated by accepted NCI criteria as "utility" can promote research efforts in the United States and is unequivocally essential if those efforts are to obtain even a modest modicum of success.

BRIEF SUMMARY OF THE INVENTION

The synthesis of potentially useful peptides presents one of the most essential and promising approaches to new types of anticancer and immunosuppressant drugs.

Tube-inhabitating marine animals of the genus Cephalodiscus (one of two divisions on the class Peterobranchia, Hemichordata Phylum) are rarely encountered. Only some eighteen species are presently known, and confined primarily to Antarctica. One Southern Hemisphere temperate region species *Cephalodiscus gilchristi* was recorded off the coast of South Africa in 1906 and described in more detail in 1915–17. In 1988 results from the first chemical study of this genus and isolation of the powerful (P388 $ED_{50} 10^{-7}$ to $10^{-9}$ μg/mL) cell growth inhibitor cephalostatin 1 from *C. gilchristi* were summarized. (See: Pettit et al., J. Am. Chem. Soc 1988 110,2006.) Subsequently cephalostatin 2–4 and 5–6 where introduction of an aromatic C'-ring (cf., 2 corresponding to cephalostatin 6) was found to greatly reduce (P388 $ED_{50}$ '$10^{-2}$ μg/mL) cytostatic activity were discussed. Further detailed investigation of *C. gilchristi* antineoplastic constituents has led to the discovery of three new and remarkable cephalostatins, herein denominated "cephalostatin 7", "cephalostatin 8", and "cephalostatin 9", which exhibit very strong and selective activity against an important panel of human cancer cell lines employed by the U.S. National Cancer Institute.

These new substances have been isolated from *Cephalodiscus gilchristi*, structurally elucidated, and found to have a confirmed active level against the U.S. National Cancer Institute's murine P388 lymphocytic leukemia (PS system) and other NCI cell lines. These substances are herein denominated "cephalostatin 7", "cephalostatin 8" and "cephalostatin 9". Cephalostatins 7–9 have the following structures:

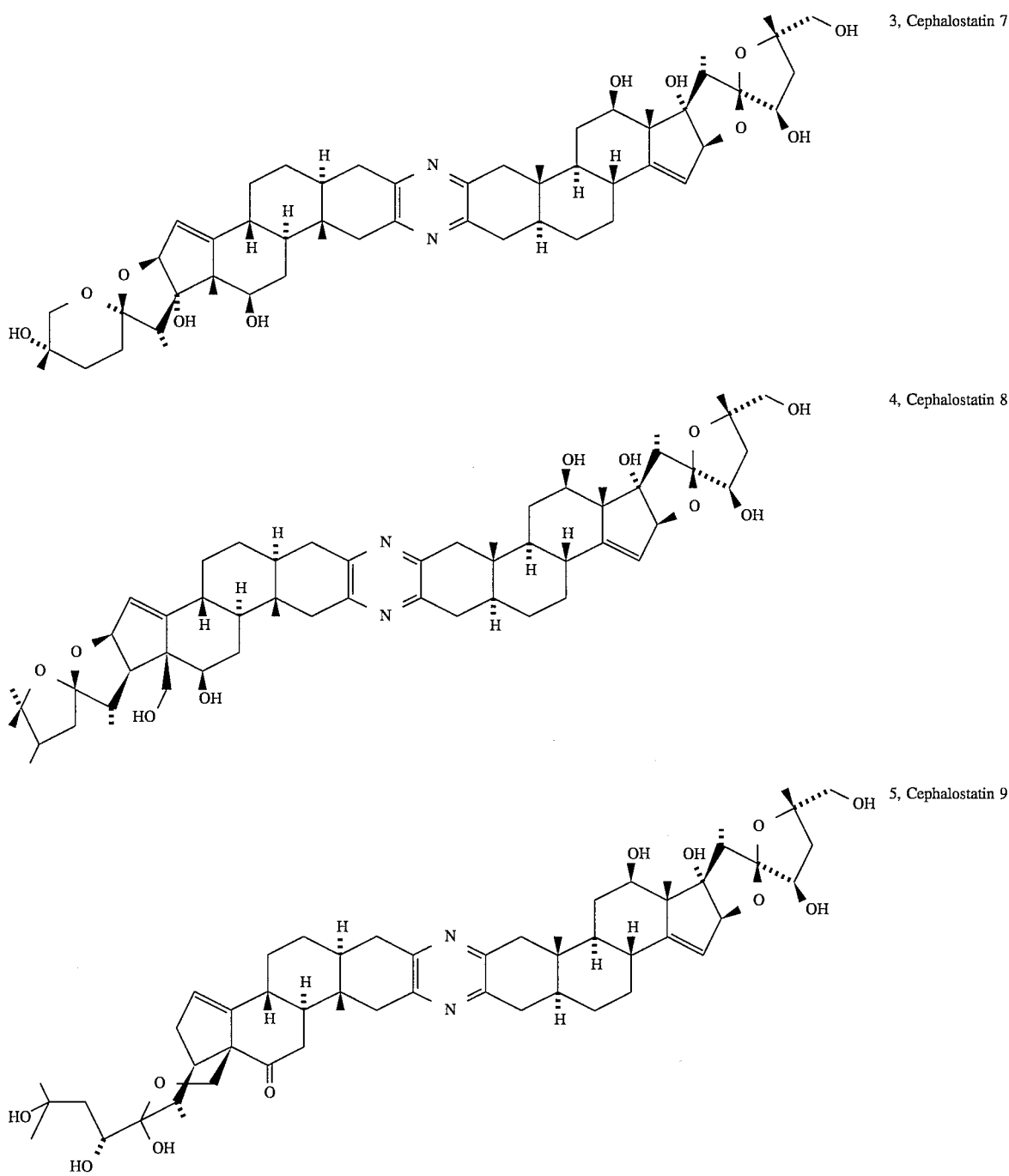

Accordingly, a primary objective of the subject invention is the isolation of new compositions of matter herein denominated "cephalostatin 7", "cephalostatin 8", and "cephalostatin 9".

Another object of the subject invention is to provide the accurate elucidation of the structures herein denominated "cephalostatin 7", "cephalostatin 8", and "cephalostatin 9".

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

DESCRIPTION OF PREFERRED EMBODIMENT

General Methods

All solvents employed for chromatographic purposes were redistilled. Column chromatography was performed using either SEPHADEX LH-60, from Pharmacia Fine Chemicals, AB, Uppsala, Sweden, or SILICA GEL (70–230 mesh) from E. Merck, Darmstadt. The HPLC columns (9.4×500 mm) employed were the PARTISIL-10 M-9-ODS-2 (C-18 reversed phase) and PARTISIL-10 M-9 columns from Whatman, Inc., Clifton, N.J. An ALTEX HPLC unit with System Controller Model 420 and Model 110A pumps was utilized for final separations. SILICA GEL GF UNIPLATES were obtained from Analtech, Inc., Newark, Del. All TLC plates were developed by UV light and/or detected by anisaldehyde-acetic acid-sulfuric acid spray (plates heated to about 150° C. for 5 to 10 min). Fractions were collected with either GILSON FC-80 (microfractionator) or FC-220 (racetrack fractionator) equipment in conjunction with a GILSON UV monitor Model HM.

All melting points are uncorrected and were observed with a Kofler-type melting point apparatus. Ultraviolet spectra (methanol solution) were recorded with a HEWLETT-PACKARD 8450A UV/VIS spectrometer. Optical rotations (methanol solution) were observed using a PERKIN-ELMER Model 214 polarimeter. Mass spectra were determined with a MAT-312 mass spectrometer. Infrared spectra (KBr) were obtained with a NICOLET FTIR Model MX-1 spectrometer. The NMR spectra were measured with a BRUKER WH-400 instrument, and deuteriopyridine was employed as solvent with tetramethylsilane as internal standard.

Animal Collection and Preliminary Experiments

In 1972, *Cephalodiscus gilchristi* (Chordata phylum, Hemichordata subphylum, Petrobaranchia class) was collected in False Bay, Cape Province, Republic of South Africa. All subsequent recollections were also taken from the same general area.

The initial sample of *Cephalodiscus gilchristi* was preserved in aqueous ethanol. Removal of solvent gave an extract that reached a confirmed level of activity against the National Cancer Institute's murine P388 lymphocytic leukemia (PS system) with a response of T/C 141 at 25 mg/kg.

Animal Extractions

The aqueous 2-propanol extract of the 1975 recollection was concentrated and partitioned between $CH_2Cl_2$ and water. The residual animal matter was extracted with 1:1 $CH_2Cl_2$-MeOH. Sufficient water was added to create two phases and the $CH_2Cl_2$ layer was separated and concentrated. The extraction procedure was repeated by adding sufficient MeOH to the MeOH-water and animal mixture to form a single phase. Again water was added to separate the $CH_2Cl_2$ which was collected and concentrated.

Solvent Partition Sequence

The $CH_2Cl_2$ extract was dissolved in 9:1 MeOH-water and extracted with hexane. The MeOH-water phase was diluted to 4:1 MeOH-water and extracted with $CCl_4$. The MeOH-water phase was diluted to 3:2 and extracted with $CH_2Cl_2$. The resulting hexane (133 g), $CCl_4$ (42 g), $CH_2Cl_2$ (28 g), and MeOH-water (62 g) fractions were concentrated and aliquots submitted for bioassay. Antineoplastic activity (PS in vitro $ED_{50}$ $4.5\times10^{-2}$ and $<1.0\times10^{-2}$) resided in the $CCl_4$ and $CH_2Cl_2$ fractions, respectively.

Isolation of the Cephalostatins

The $CCl_4$ and $CH_2Cl_2$ active fractions as shown in Scheme Part 1 were chromatographed on a column of SILICA GEL using a gradient elution from hexane-EtOAc to EtOAc-MeOH-water. The procedure was repeated until the total fractions were separated by this procedure. The principal in vitro active fraction B was further separated by a gel permeation procedure using SEPHADEX LH-60 and 10:10:1 hexane-$CH_2Cl_2$-MeOH. Recombination of fractions on the basis of TLC properties, led to the principal in vitro active fraction D. Fraction D (2.53 g) was next separated by SILICA GEL chromatography using gradient elution hexane-EtOAc-MeOH (10:10:0 to 4). By means of 12 ml fractions, 4000 ml was collected and of these, fractions noted as E and F in Scheme 1, Part 2 were found to give the highest level of antineoplastic activity. At this point, active fractions E and F from the $CH_2Cl_2$ extract were combined with the corresponding ones from the $CCl_4$ extract as shown in Scheme 1, Part 3. Extensive separation of the most active fractions E and F by further SILICA GEL column chromatography using gradient elution (hexane-$CH_2Cl_2$-MeOH 10:10:0.5 to 4.0) in 7 ml fractions (500 ml total) afforded four active fractions G, H, I, and J. Fractions H and I were combined on the basis of TLC properties. The entire sequence is shown in Scheme 1, below.

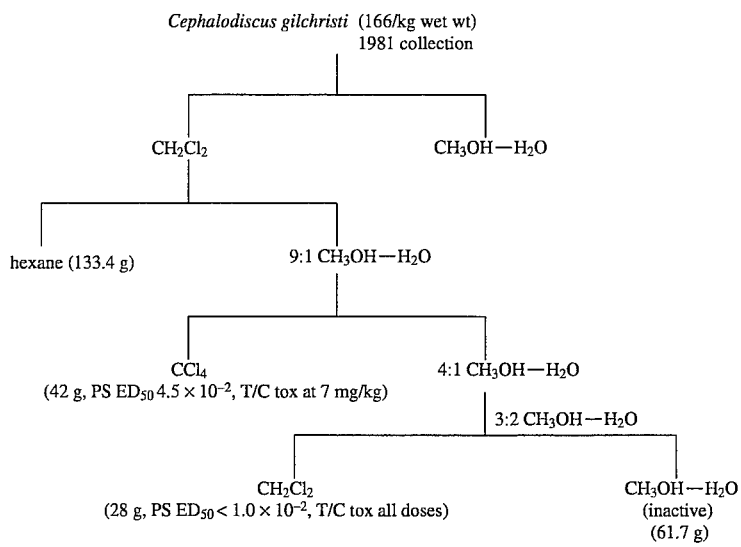
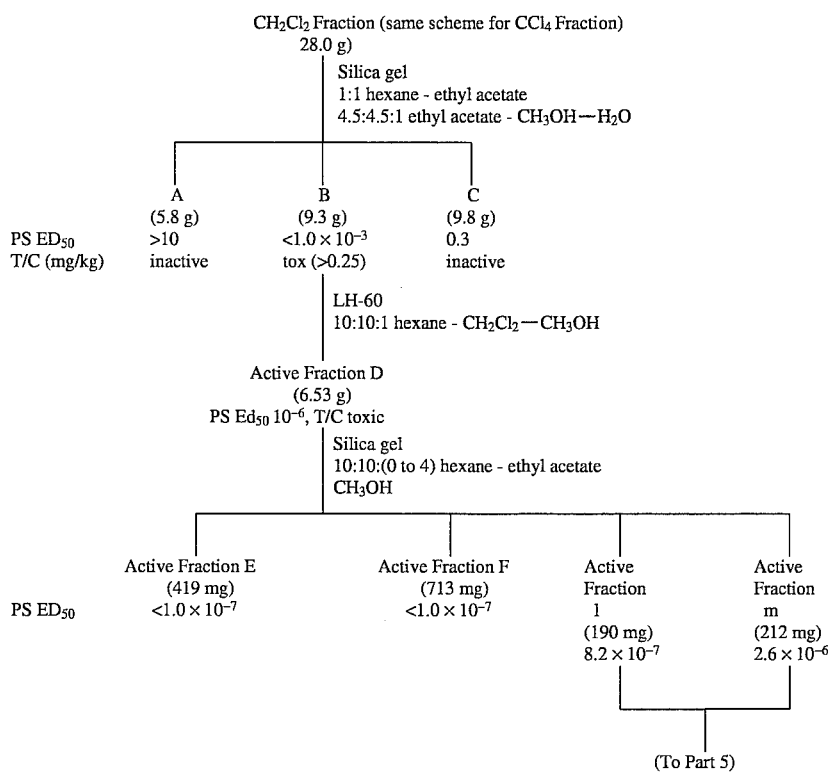

Separation Scheme Part 3

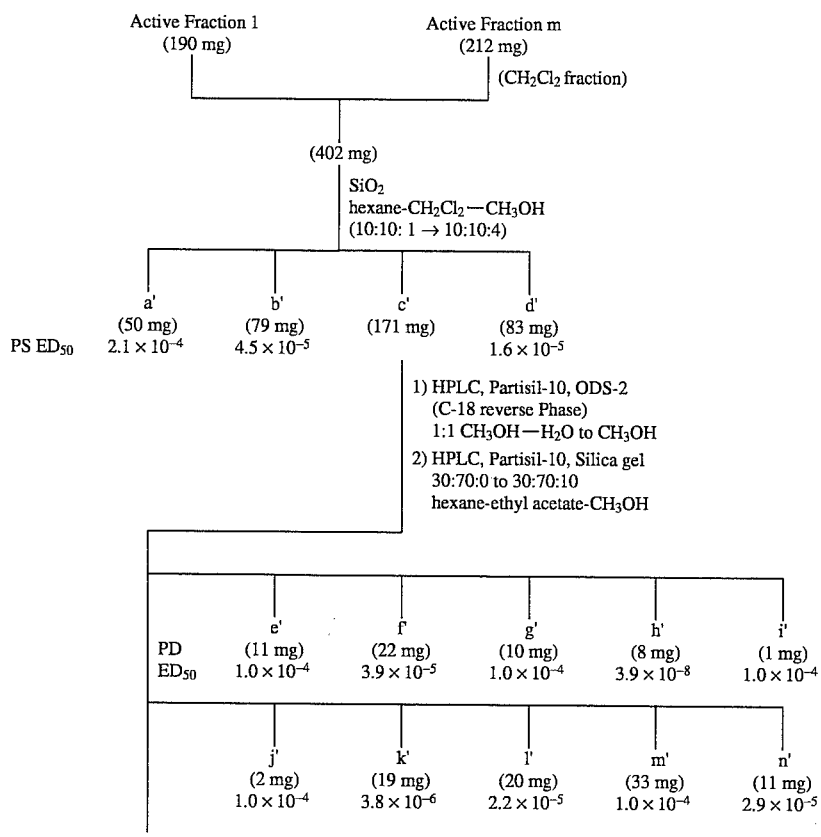

Separation Scheme Part 4

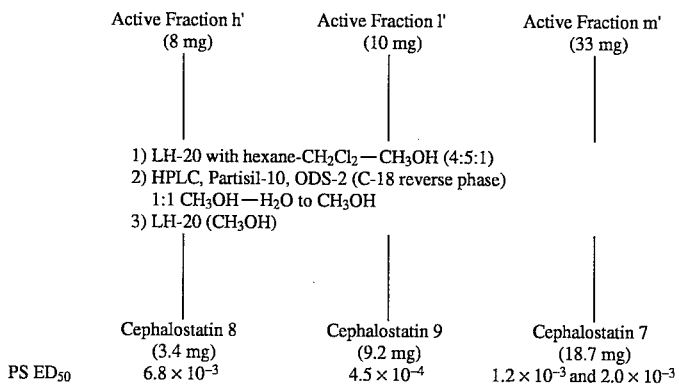

Fractions G to J were still quite complex and required extensive HPLC methods of separation. A solution of fraction G in 1:1 MeOH-water was chromatographed using HPLC techniques with a C-18 reverse phase column and a flow rate of 2.0 ml/min with a gradient to methanol. The fraction with the most promising PS activity was further separated by HPLC using a SILICA GEL column and hexane-EtOAc-MeOH gradient (30:70:0 to 10) as mobile phase with a flow rate of 2.0 ml/min. By this means 136 mg of cephalostatin 1 was isolated. Fractions H, I and J were further separated in a procedure analogous to that used for fraction G, to yield cephalostatin 3 (18 mg), cephalostatin 2 (240 mg) and active fraction K (13 mg). Fraction K was further purified by SEPHADEX LH-20 using hexane-$CH_2CH_2$-MeOH 4:5:1 and HPLC to yield cephalostatin 4 (8 mg).

A 28 g methylene chloride fraction prepared from 166 kg (wet wt) of *C. gilchristi* was separated (P388 lymphocytic leukemia cell line guided) to provide fractions h (8 mg), l (20 mg) and m (30 mg) using a series of stearic exclusion and partition chromatographic procedures followed by gradient HPLC, as shown in Scheme 1, part 4 and using the technique previously described by Pettit et al. in *Can. J. Chem.*, 1988, 1509 and incorporated herein by this references thereto. Continued bioassay directed separation of fraction m employing a gel (SEPHADEX LH-20)-partition→HPLC→gel permeation sequence afforded (18.7 mg, $1.1\times10^{-6}\%$ yield) cephalostatin 7, an amorphous powder, dp 315° C.; Rf 0.39 (SiO$_2$) in 90:10:0.8 CH$_2$Cl$_2$:CH$_3$OH:H$_2$O; $[\alpha]_D$+106° C. (c, 0.244 in CH$_3$OH); SP-SIMS$^{12}$, 967.5067 [M+K]$^+$for C$_{54}$H$_{76}$N$_2$O$_{11}$ (calcd. 967.6413 and 928.5450 for M$^+$); UV (CH$_3$OH)$V_{max}$286 ($\epsilon$ 17,400) and 310 (shoulder) nm; and IR (KBr) 3430, 2960, 2920, 2880, 2860, 1715 (weak, broad), 1650–1615 (broad), 1450, 1400, 1385, 1056, 1043 and 950 cm-1; for the $^1$H-and $^{13}$C-NMR as shown in Table I below.

TABLE 1

$^1$H and $^{13}$C—NMR assignments for cephalostatin 7 in pyridine-d$_5$

| Position | "Right-side" $^{13}$C | $^1$H (mult, J in Hz) | "Left-side" $^{13}$C | $^1$H (mult, J in Hz) |
|---|---|---|---|---|
| 1a | 46.04 | 3.08 (d, 16.7) | 46.03 | 3.08 (d, 18.0 |
| 1b |  | 2.61 |  | 2.61 |
| 2 | 148.86 |  | 148.86 |  |
| 3 | 148.58 |  | 148.58 |  |
| 4a | 35.78 | 2.89 (dd, 17.6, 4.0) | 35.78 | 2.89 (dd, 17.6, 4.0) |
| 4b |  | 2.66 |  | 2.60 |
| 5 | 41.79 | 1.56 | 41.79 | 1.56 |
| 6a | 28.27 | 1.48 | 28.27 | 1.48 |
| 6b |  | 1.20 |  | 1.20 |
| 7a | 28.67 | 1.63 | 28.95 | 1.55 |
| 7b |  | 1.42 |  | 1.31 |
| 8 | 33.79 | 2.04 | 34.02 | 2.06 |
| 9 | 53.22 | 0.88 (dt, 3.5, 11.2) | 52.92 | 0.98 (dt, 4.0, 11.8) |
| 10a | 36.32 |  | 36.32 |  |
| 11a | 28.95 | 2.04 | 29.19 | 2.08 |
| 11b |  | 1.72 (q, 12.0) |  | 1.75 |
| 12 | 75.59 | 4.05 (ddd, 12.0, 5.2, 1.0) | 75.66 | 4.17 (ddd, 11.9, 5.0, 1.0) |
| 13 | 55.39 |  | 56.02 |  |
| 14 | 152.73 |  | 154.85 |  |
| 15 | 122.25 | 5.64 (s) | 119.97 | 5.60 (s) |
| 16 | 93.16 | 5.24 (s) | 93.74 | 5.17 (s) |
| 17 | 91.66 |  | 93.31 |  |
| 18 | 12.56 | 1.31 (s, 3H) | 13.00 | 1.31 (s, 3H) |
| 19 | 11.74 | 0.75 (s, 3H) | 11.74 | 0.76 (s, 3H) |
| 20 | 44.50 | 2.83 (q, 7.0) | 48.45 | 2.19 |
| 21 | 9.01 | 1.33 (d, 7.0, 3H) | 8.14 | 1.26 (d, 6.8, 3H) |
| 22 | 117.17 |  | 107.90 |  |
| 23a | 71.51 | 4.79 (dd, 15.2, 8.0) | 27.72 | 2.53(dt, 4.9, 13.3) |
| 23b |  |  |  | 1.52 |
| 24a | 39.53 | 2.71 (dd, 11.5, 8.0) | 33.28 | 2.11 |
| 24b |  | 2.34 (t, 10.9) |  | 1.85 |
| 25 | 82.81 |  | 65.76 |  |
| 26a | 69.28 | 3.79 (d, 11.2) | 70.18 | 3.98 (d, 11.4) |
| 26b |  | 3.70 (d, 11.3) |  | 3.57 (dd, 11.2, 1.0) |
| 27 | 26.42 | 1.61 (s, 3H) | 26.99 | 1.23 (d, 3H) |
| 22* |  |  |  | 20, 23a, 26a, 26b |
| 24* |  |  |  | 23a, 27 |
| 25* |  |  |  | 26a, 26b, 27 |
| 26* |  |  |  | 27 |

*Selected HMBC correlations for the modified "left-side"

Analogous preparation of fraction h and 1 provided (3.4 mg, $2\times10^{-7}\%$ yield and 9.2 mg, $5.5\times10^{-7}\%$ recovery, respectively) cephalostatins 8, a powder, dp 313 ° C. R$_f$ 0.35 (SiO$_2$) in 90:10:0.8 CH$_2$Cl$_2$:CH$_3$OH:H$_2$O; $[\alpha]_d$ +110° C. (c, 0.10 in CH$_3$OH); SP-SIMS$^{12}$, 965.5261 [M+K]$^+$for C$_{54}$H$_{78}$N$_2$O$_{11}$ (calcd. 965.6640 and 926.5657 for M$^+$); UV (CH$_3$OH) $V_{max}$ 286 ($\epsilon$ 20,800) 310 (shoulder) nm; and IR (KBr) 3400, 2970, 2920, 2880, 2860, 1715 (weak, broad), 1650–1600 (broad), 1445, 1400, 1385, 1037 and 965 cm$^{-1}$; and cephalostatins 9 (5); powder, dp 307° C.; R$_f$ 0.38 (SiO$_2$) 90:10:08 CH$_2$Cl$_2$:CH$_3$OH:H$_2$O; $[\alpha]_D$+105° C. (c, 0.496 in CH$_3$OH); SP-SIMS$^{12}$ , found, 929.5527 [M+K]$^+$ for C$_{54}$H$_{76}$N$_2$O$_{11}$ (calcd. 929.5527 and 928.5450 for M$^+$); UV (CH$_3$OH) V$_{max}$ 286 ($\epsilon$ 18,600) and 310 (shoulder) nm; and IR (KBr) 3400, 2990, 2930, 2880, 2860, 1710 (string, sharp), 1645–1630 (broad), 1445, 1400, 1385, 1055 and 950 cm-1.

With the x-ray crystal structure of cephalostatin I (See: *J. Am. Chem. Soc.* 1988, 110,2006) and the corresponding $^1$H- and $^{13}$C-NMR assignments providing a solid foundation for related structural determinations, the structures shown above were assigned, respectively, to cephalostatin 7–9. While the right-side moiety of pyridizines 7–9 proved identical with that of cephalostatins 1, substantial differences existed in each of the three beyond the left-side C'-ring. The structural elucidation of cephalostatin 7, primarily by high field two-dimensional $^1$H- and $^{13}$C-NMR (Table 1) provides an appropriate illustration. Partial structure A for rings D'-F' was derived from the result of heteronuclear multiple bond correlations (HMBC) as described by Bax et al., *J. Am. Chem. Soc.*, 1986, 108,2094. Application of comparable H,H-relayed COSY nOe, and HMBC experiments to cephalostatin 8 resulted in the illustrated structure as most consistent with the spectral data with only the stereochemistry at C-22' remaining equivocal. The same approach was also successful with cephalostatin 9 excepting the stereochemistry at C-22'. The configuration of the C-23' hydroxyl is likely R as shown, and established in cephalostatin 1.

Discovery of cephalostatins 7–9 with such potent and selective cytostatic activity against certain human cancer cell lines suggests that the pyridizine right-side unit is probably the key to these promising biological properties. Minor configuration and substitution (including an additional methyl in cephalostatin 8) alterations in the left-side E'- and F'- rings appear well tolerated, but not aromatization of the C'-ring with concomitant bonding to the side-chain system.

Cephalostatins 7–9 displayed remarkable potency with GI$_{50}$ (molar) values of 10$^{-9}$, 10$^{-10}$ against a number of cell lines including non-small cell lung HOP62, small cell lung DMS-273, renal RXF-393, brain U-251, brain SF-295 and leukemia CCRF-CEM, HL60 and RPM1-8226. GI$_{50}$ Values of 10$^{-8}$ –10$^{-9}$ were obtained for the breast MCF-7 cell line. Significant TCI means were also displayed. The "means graphs" as described and interpreted by Boyd et al. in "Data display and analysis strategies from the NCI disease oriented in vitro antitumor drug screen" in Valeriote et al. *Antitumor Drug Discovery and Development*; Klusoer Academic Press, Amsterdam, 1991, for cephalostatin 7–9 show a remarkably similar pattern of relative cellular sensitivity across the panel of 60 cell lines.

Example 1
Cephalostatin 7

National Cancer Institute Developmental Therapeutics Program  
Mean Graphs  
NSC: 378736-C   Units:  
Report Date: May 17, 1990

| Panel/Cell Line | Log$_{10}$ GI50 | Mean Log$_{10}$ GI50 |
|---|---|---|
| Leukemia | | |
| CCRF-CEM | −8.77 | |
| HL-60 TB | <−9.44 | |
| K562 | −7.99 | |
| MOLT-4 | −8.85 | |
| RPMI-8226 | <−9.44 | |
| Non-Small Cell Lung Cancer | | |
| A-549 | −8.55 | |
| EKVX | −8.28 | |
| HOP-18 | −6.14 | |
| HOP-62 | −9.41 | |
| HOP-92 | −8.64 | |
| NCI-H226 | −7.97 | |
| NCI-H23 | −8.51 | |
| NCI-H460 | −8.87 | |
| NCI-H522 | −7.88 | |
| Small Cell Lung Cancer | | |
| DMS-114 | −9.09 | |
| DMS-273 | <−9.44 | |
| Colon Cancer | | |
| COLO-205 | −7.85 | |
| DLD-1 | −7.09 | |
| HCC-2998 | −6.40 | |
| HCT-116 | −7.56 | |
| HCT-15 | −8.04 | |
| HT-29 | −8.75 | |
| KM-12 | −7.35 | |
| KM-20L2 | −8.54 | |
| SW-620 | −8.03 | |
| CNS Cancer | | |
| SF-268 | −8.33 | |
| SF-295 | <−9.44 | |
| SF-539 | −8.52 | |
| SNB-19 | −7.39 | |
| SNB-75 | <−9.44 | |
| SNB-78 | −8.82 | |
| U-251 | −9.37 | |
| XF-498 L | −8.31 | |

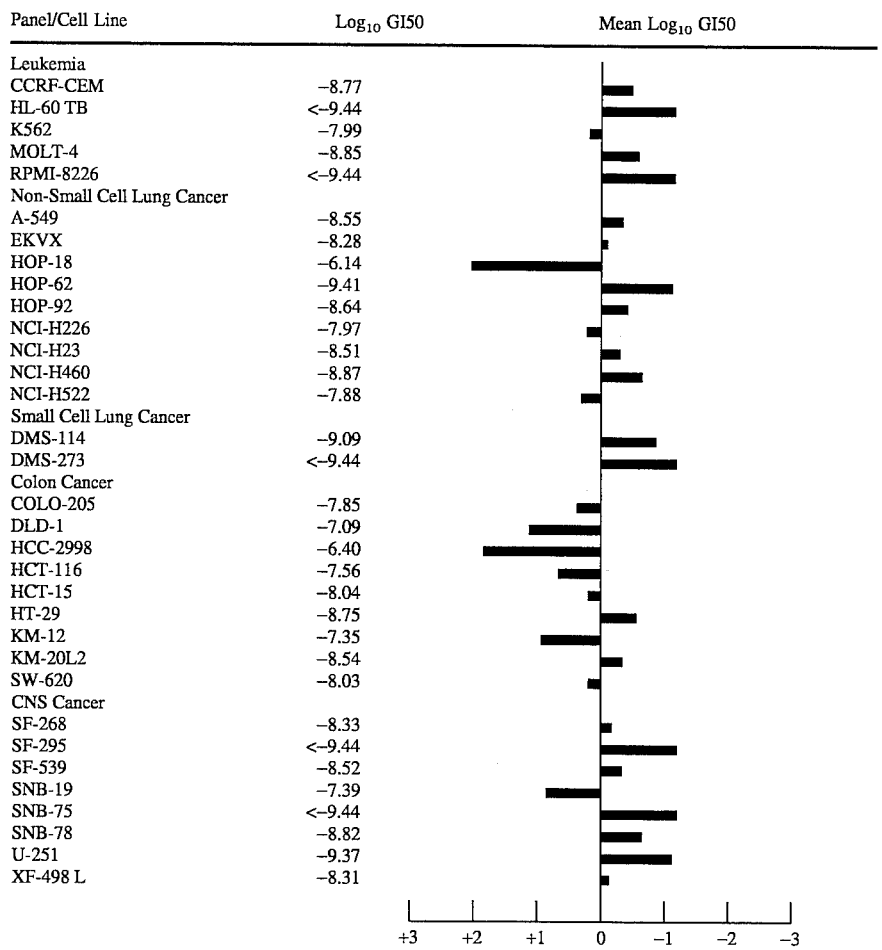

-continued

Example 1
Cephalostatin 7

National Cancer Institute Developmental Therapeutics Program  NSC: 378736-C   Units:
Mean Graphs  Report Date: May 17, 1990

| Panel/Cell Line | $Log_{10}$ GI50 | Mean $Log_{10}$ GI50 |
|---|---|---|
| Melanoma | | |
| LOX-IMVI | −7.97 | |
| MALME-3M | −8.00 | |
| M19-MEL | −6.47 | |
| SK-MEL-2 | −8.35 | |
| SK-MEL-5 | −7.78 | |
| UACC-257 | −7.58 | |
| UACC-62 | −8.41 | |
| Ovarian Cancer | | |
| IGROV-1 | −8.08 | |
| OVCAR-3 | −6.36 | |
| OVCAR-4 | −7.04 | |
| OVCAR-5 | −8.23 | |
| OVCAR-8 | −6.37 | |
| SK-OV-3 | −8.75 | |
| Renal Cancer | | |
| A498 | −8.97 | |
| CAKI-1 | −7.71 | |
| RXF-393 L | <−9.44 | |
| SN-12C | −6.38 | |
| SN12K1 | <−9.44 | |
| UO-31 | −7.99 | |
| Miscellaneous | | |
| MCF-7 | −8.02 | |
| MCF-7/ADR | −6.21 | |
| P388 | <−9.44 | |
| P388/ADR | −8.95 | |
| | | |
| Mean | −8.19 | |
| Delta | 1.25 | |
| Range | 3.30 | |

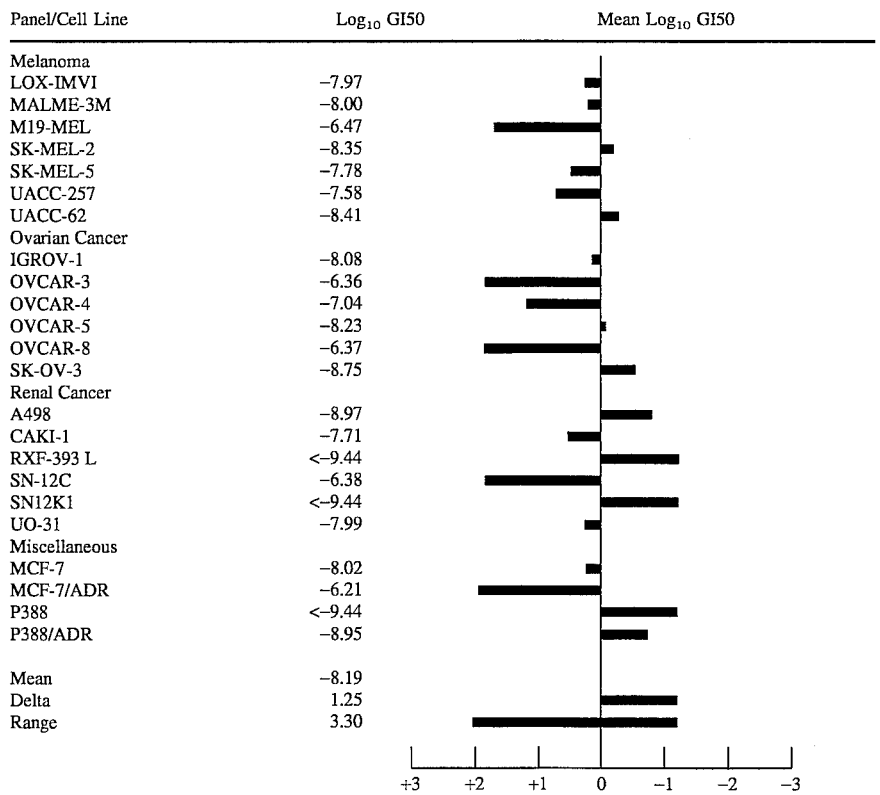

Example 1
Cephalostatin 7

National Cancer Institute Developmental Therapeutics Program  
Mean Graphs  
NSC: 378736-C     Units:  
Report Date: May 17, 1990

| Panel/Cell Line | Log$_{10}$ GI50 | Mean Log$_{10}$ GI50 |
|---|---|---|
| Leukemia | | |
| CCRF-CEM | −7.74 | |
| HL-60 TB | −7.33 | |
| K562 | −6.35 | |
| MOLT-4 | −6.00 | |
| RPMI-8226 | | |
| Non-Small Cell Lung Cancer | | |
| A-549 | −6.15 | |
| EKVX | −6.34 | |
| HOP-18 | −5.77 | |
| HOP-62 | −8.63 | |
| HOP-92 | −7.47 | |
| NCI-H226 | −6.09 | |
| NCI-H23 | −7.42 | |
| NCI-H460 | −7.41 | |
| NCI-H522 | −7.09 | |
| Small Cell Lung Cancer | | |
| DMS-114 | −7.74 | |
| DMS-273 | −8.83 | |
| Colon Cancer | | |
| COLO-205 | −7.28 | |
| DLD-1 | −5.95 | |
| HCC-2998 | −6.07 | |
| HCT-116 | −6.31 | |
| HCT-15 | −7.12 | |
| HT-29 | −7.42 | |
| KM-12 | −6.24 | |
| KM-20L2 | −7.05 | |
| SW-620 | −7.29 | |
| CNS Cancer | | |
| SF-268 | −6.90 | |
| SF-295 | −9.09 | |
| SF-539 | −7.38 | |
| SNB-19 | −6.09 | |
| SNB-75 | −8.70 | |
| SNB-78 | −6.51 | |
| U-251 | −7.42 | |
| XF-498 L | −7.44 | |

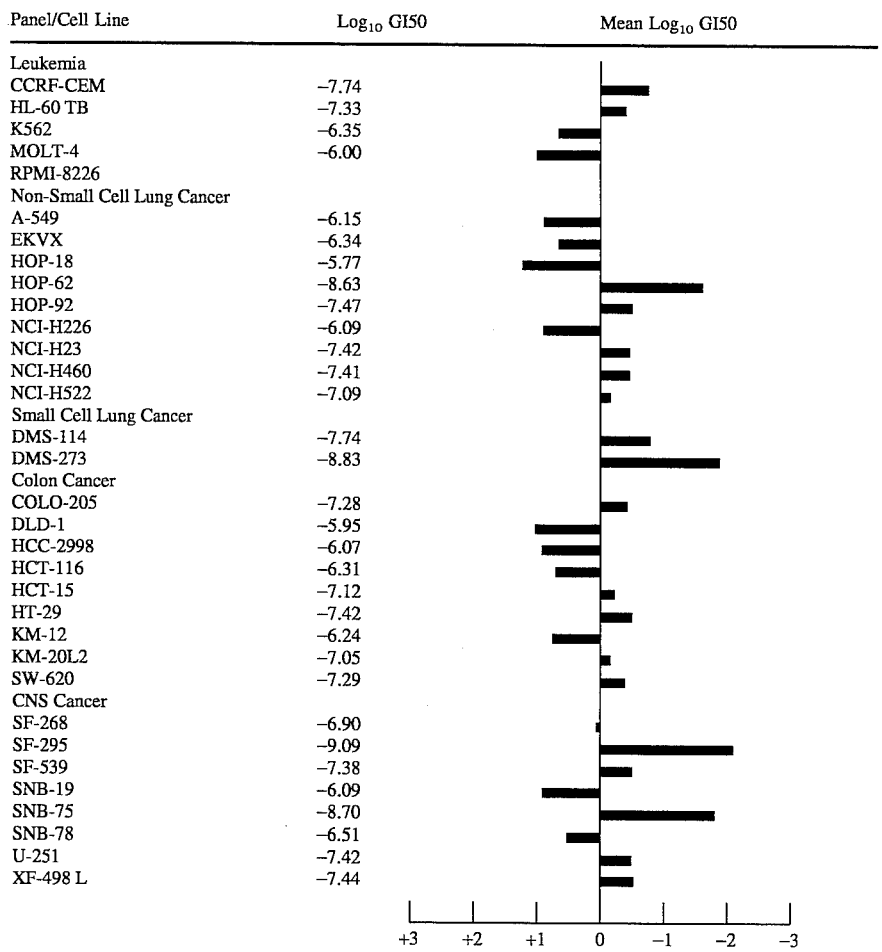

Example 1
Cephalostatin 7

National Cancer Institute Developmental Therapeutics Program  
Mean Graphs  
NSC: 378736-C  Units:  
Report Date: May 17, 1990

| Panel/Cell Line | $\text{Log}_{10}$ GI50 | Mean $\text{Log}_{10}$ GI50 |
|---|---|---|
| Melanoma | | |
| LOX-IMVI | −6.44 | |
| MALME-3M | −7.16 | |
| M19-MEL | −6.10 | |
| SK-MEL-2 | −7.38 | |
| SK-MEL-5 | −7.08 | |
| UACC-257 | −7.07 | |
| UACC-62 | −7.97 | |
| Ovarian Cancer | | |
| IGROV-1 | −6.23 | |
| OVCAR-3 | −5.95 | |
| OVCAR-4 | −6.09 | |
| OVCAR-5 | −7.26 | |
| OVCAR-8 | −5.92 | |
| SK-OV-3 | −7.71 | |
| Renal Cancer | | |
| A498 | −7.37 | |
| CAKI-1 | −6.18 | |
| RXF-393 L | −9.41 | |
| SN-12C | −5.92 | |
| SN12K1 | −6.40 | |
| UO-31 | −7.62 | |
| Miscellaneous | | |
| MCF-7 | −6.28 | |
| MCF-7/ADR | −5.69 | |
| P388 | −6.13 | |
| P388/ADR | −5.94 | |
| | | |
| Mean | −6.94 | |
| Delta | 2.47 | |
| Range | 3.73 | |

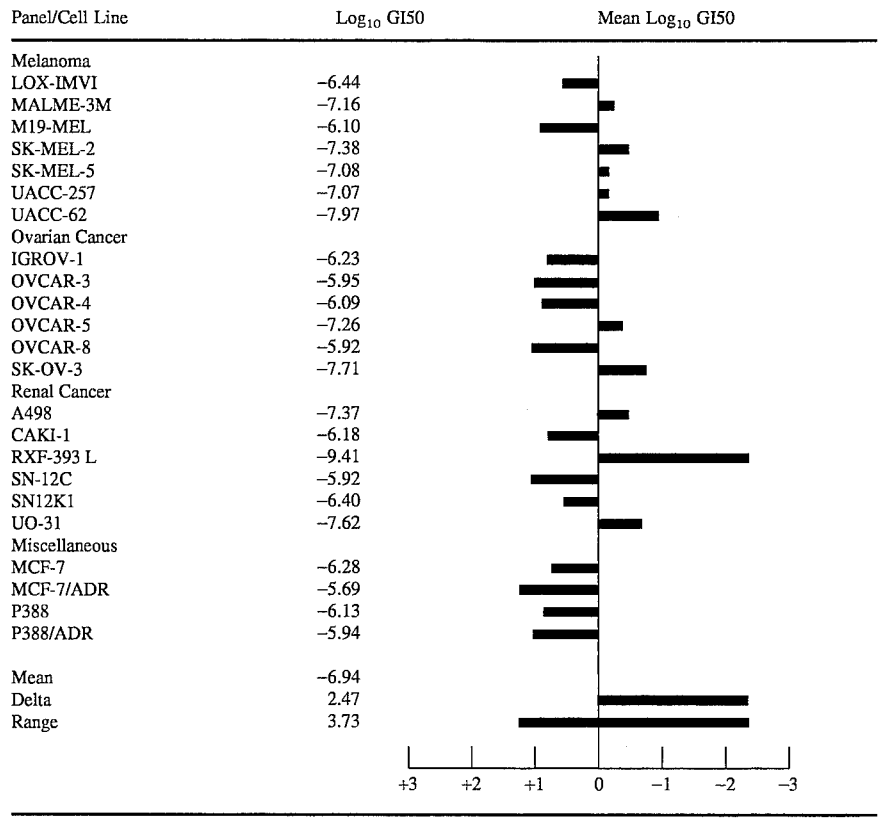

Example 2
Cephalostatin 8

National Cancer Institute Developmental Therapeutics Program
Mean Graphs

NSC: 378734-Z   Units:
Report Date: May 17, 1990

| Panel/Cell Line | Log$_{10}$ GI50 |
|---|---|
| Leukemia | |
| CCRF-CEM | −9.32 |
| HL-60 TB | <−9.44 |
| K562 | −7.76 |
| MOLT-4 | |
| RPMI-8226 | <−9.44 |
| Non-Small Cell Lung Cancer | |
| A-549 | −8.22 |
| EKVX | −7.92 |
| HOP-18 | −5.68 |
| HOP-62 | <−9.44 |
| HOP-92 | |
| NCI-H226 | −8.20 |
| NCI-H23 | |
| NCI-H460 | −9.15 |
| NCI-H522 | −7.64 |
| Small Cell Lung Cancer | |
| DMS-114 | <−9.44 |
| DMS-273 | <−9.44 |
| Colon Cancer | |
| COLO-205 | −7.37 |
| DLD-1 | −6.23 |
| HCC-2998 | −5.87 |
| HCT-116 | −7.49 |
| HCT-15 | −7.13 |
| HT-29 | −8.52 |
| KM-12 | −6.77 |
| KM-20L2 | −8.14 |
| SW-620 | −8.10 |
| CNS Cancer | |
| SF-268 | −8.52 |
| SF-295 | <−9.44 |
| SF-539 | −8.44 |
| SNB-19 | −7.58 |
| SNB-75 | <−9.44 |
| SNB-78 | <−9.44 |
| U-251 | <−9.44 |
| XF-498 L | <−9.44 |

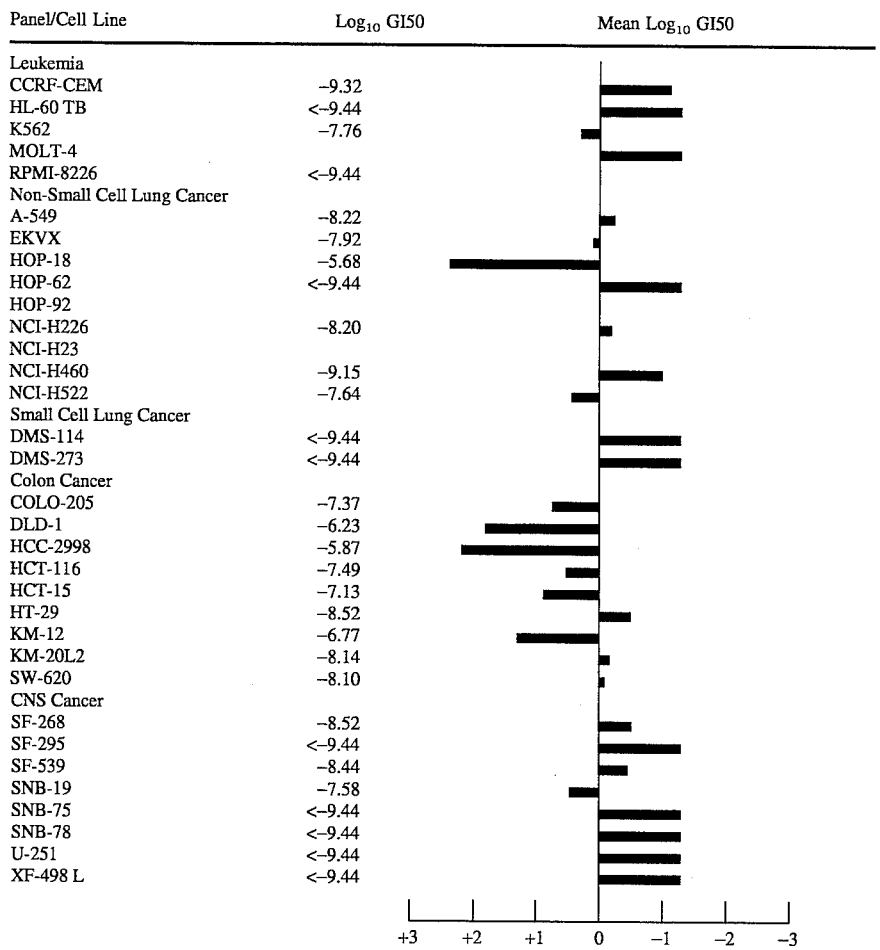

Example 2
Cephalostatin 8

National Cancer Institute Developmental Therapeutics Program  NSC: 378734-Z  Units:
Mean Graphs  Report Date: May 17, 1990

| Panel/Cell Line | $\text{Log}_{10}$ GI50 | Mean $\text{Log}_{10}$ GI50 |
|---|---|---|
| Melanoma | | |
| LOX-IMVI | −8.15 | |
| MALME-3M | −8.01 | |
| M19-MEL | −5.67 | |
| SK-MEL-2 | −7.94 | |
| SK-MEL-5 | −8.06 | |
| UACC-257 | −7.19 | |
| UACC-62 | −8.31 | |
| Ovarian Cancer | | |
| IGROV-1 | −8.31 | |
| OVCAR-3 | −5.70 | |
| OVCAR-4 | | |
| OVCAR-5 | −8.06 | |
| OVCAR-8 | >−5.44 | |
| SK-OV-3 | <−9.44 | |
| Renal Cancer | | |
| A498 | −8.39 | |
| CAKI-1 | −7.39 | |
| RXF-393 L | <−9.44 | |
| SN-12C | >−5.44 | |
| SN12K1 | <−9.44 | |
| UO-31 | −6.93 | |
| Miscellaneous | | |
| MCF-7 | −9.12 | |
| MCF-7/ADR | >−5.44 | |
| P388 | <−9.44 | |
| P388/ADR | −7.04 | |
| | | |
| Mean | −8.02 | |
| Delta | 1.42 | |
| Range | 4.00 | |

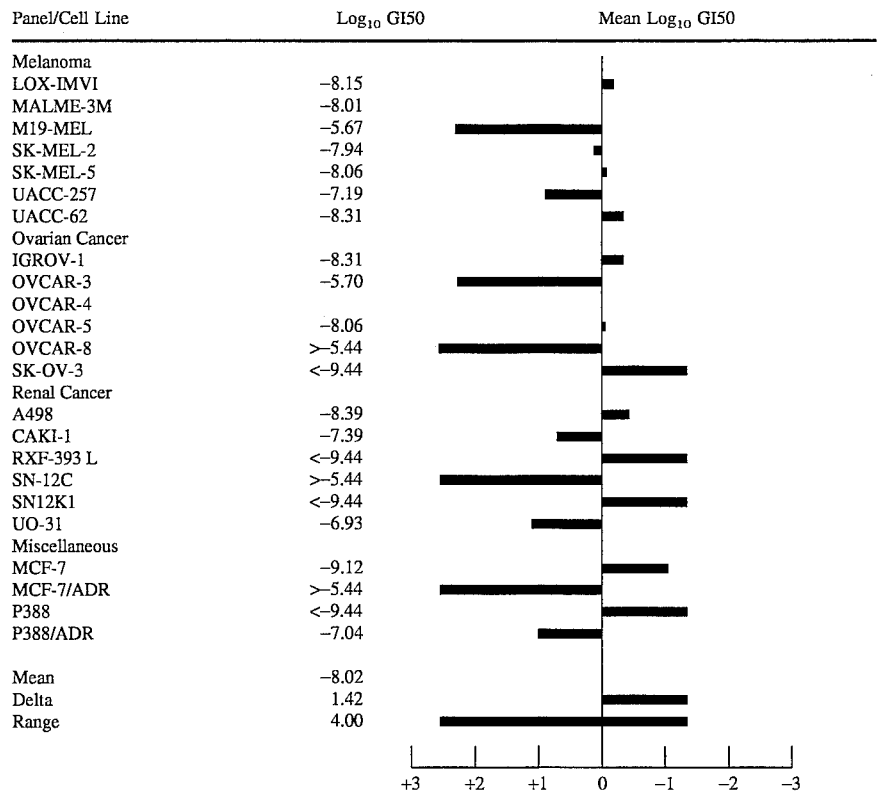

+3  +2  +1  0  −1  −2  −3

-continued

Example 2
Cephalostatin 8

National Cancer Institute Developmental Therapeutics Program  NSC: 378734-Z   Units:
Mean Graphs                                                    Report Date: May 17, 1990

| Panel/Cell Line | Log$_{10}$ GI50 | Mean Log$_{10}$ GI50 |
|---|---|---|
| Leukemia | | |
| CCRF-CEM | >−5.44 | |
| HL-60 TB | | |
| K562 | >−5.44 | |
| MOLT-4 | | |
| RPMI-8226 | >−5.44 | |
| Non-Small Cell Lung Cancer | | |
| A-549 | >−5.44 | |
| EKVX | −5.70 | |
| HOP-18 | >−5.44 | |
| HOP-62 | −8.61 | |
| HOP-92 | | |
| NCI-H226 | >−5.44 | |
| NCI-H23 | | |
| NCI-H460 | −6.98 | |
| NCI-H522 | −6.37 | |
| Small Cell Lung Cancer | | |
| DMS-114 | >−5.44 | |
| DMS-273 | −9.13 | |
| Colon Cancer | | |
| COLO-205 | −6.86 | |
| DLD-1 | >−5.44 | |
| HCC-2998 | >−5.44 | |
| HCT-116 | −5.85 | |
| HCT-15 | −6.20 | |
| HT-29 | −6.38 | |
| KM-12 | >−5.44 | |
| KM-20L2 | −6.21 | |
| SW-620 | −7.05 | |
| CNS Cancer | | |
| SF-268 | −7.01 | |
| SF-295 | −9.41 | |
| SF-539 | −6.76 | |
| SNB-19 | >−5.44 | |
| SNB-75 | −7.87 | |
| SNB-78 | −6.19 | |
| U-251 | −7.18 | |
| XF-498 L | <−9.44 | |

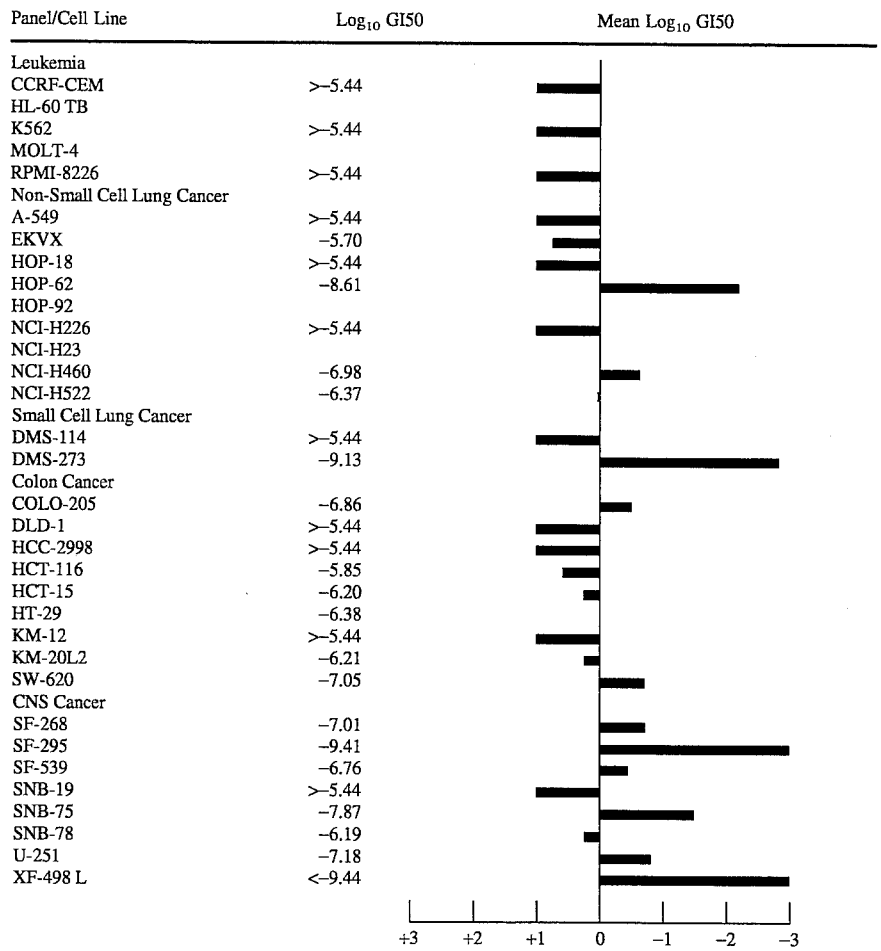

+3   +2   +1   0   −1   −2   −3

-continued

Example 2
Cephalostatin 8

National Cancer Institute Developmental Therapeutics Program  NSC: 378734-Z  Units:
Mean Graphs  Report Date: May 17, 1990

| Panel/Cell Line | Log$_{10}$ GI50 | Mean Log$_{10}$ GI50 |
|---|---|---|
| Melanoma | | |
| LOX-IMVI | >−5.44 | |
| MALME-3M | −6.74 | |
| M19-MEL | >−5.44 | |
| SK-MEL-2 | −6.55 | |
| SK-MEL-5 | −6.80 | |
| UACC-257 | −6.41 | |
| UACC-62 | −7.13 | |
| Ovarian Cancer | | |
| IGROV-1 | >−5.44 | |
| OVCAR-3 | >−5.44 | |
| OVCAR-4 | | |
| OVCAR-5 | −6.97 | |
| OVCAR-8 | >−5.44 | |
| SK-OV-3 | −7.65 | |
| Renal Cancer | | |
| A498 | −6.78 | |
| CAKI-1 | −>5.44 | |
| RXF-393 L | −9.30 | |
| SN-12C | >−5.44 | |
| SN12K1 | >−5.44 | |
| UO-31 | −6.54 | |
| Miscellaneous | | |
| MCF-7 | −6.30 | |
| MCF-7/ADR | >−5.44 | |
| P388 | >−5.44 | |
| P388/ADR | >−5.44 | |
| Mean | −6.39 | |
| Delta | 3.05 | |
| Range | 4.00 | |

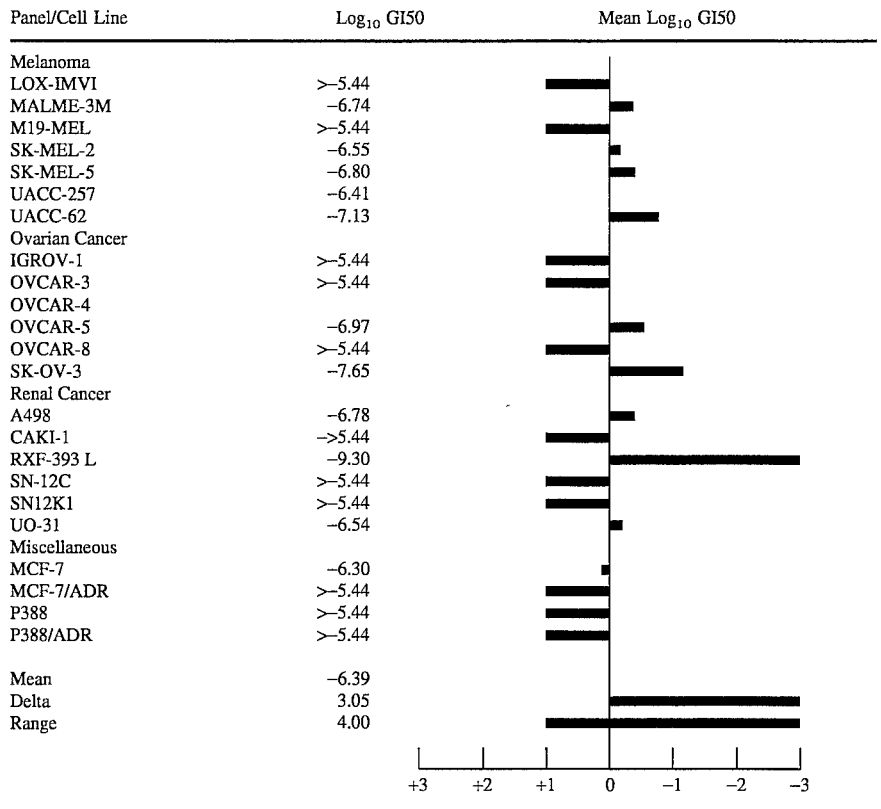

+3   +2   +1   0   −1   −2   −3

Example 3
Cephalostatin 9

National Cancer Institute Developmental Therapeutics Program  NSC: 378735-A    Units:
Mean Graphs  Report Date: May 17, 1990

| Panel/Cell Line | Log$_{10}$ GI50 | Mean Log$_{10}$ GI50 |
|---|---|---|
| Leukemia | | |
| CCRF-CEM | −9.12 | |
| HL-60 TB | <−9.44 | |
| K562 | −7.95 | |
| MOLT-4 | −8.80 | |
| RPMI-8226 | <−9.44 | |
| Non-Small Cell Lung Cancer | | |
| A-549 | −8.51 | |
| EKVX | −9.41 | |
| HOP-18 | −6.57 | |
| HOP-62 | −9.30 | |
| HOP-92 | −8.39 | |
| NCI-H226 | −8.21 | |
| NCI-H23 | −8.51 | |
| NCI-H460 | −8.82 | |
| NCI-H522 | −7.34 | |
| Small Cell Lung Cancer | | |
| DMS-114 | −9.29 | |
| DMS-273 | <−9.44 | |
| Colon Cancer | | |
| COLO-205 | −7.82 | |
| DLD-1 | −6.95 | |
| HCC-2998 | −7.61 | |
| HCT-116 | −7.64 | |
| HCT-15 | −7.83 | |
| HT-29 | −8.34 | |
| KM-12 | −7.74 | |
| KM-20L2 | −8.16 | |
| SW-620 | −8.03 | |
| CNS Cancer | | |
| SF-268 | −8.17 | |
| SF-295 | <−9.44 | |
| SF-539 | −8.70 | |
| SNB-19 | −7.44 | |
| SNB-75 | <−9.44 | |
| SNB-78 | −8.84 | |
| U-251 | <−9.44 | |
| XF-498 L | −8.62 | |

+3  +2  +1  0  −1  −2  −3

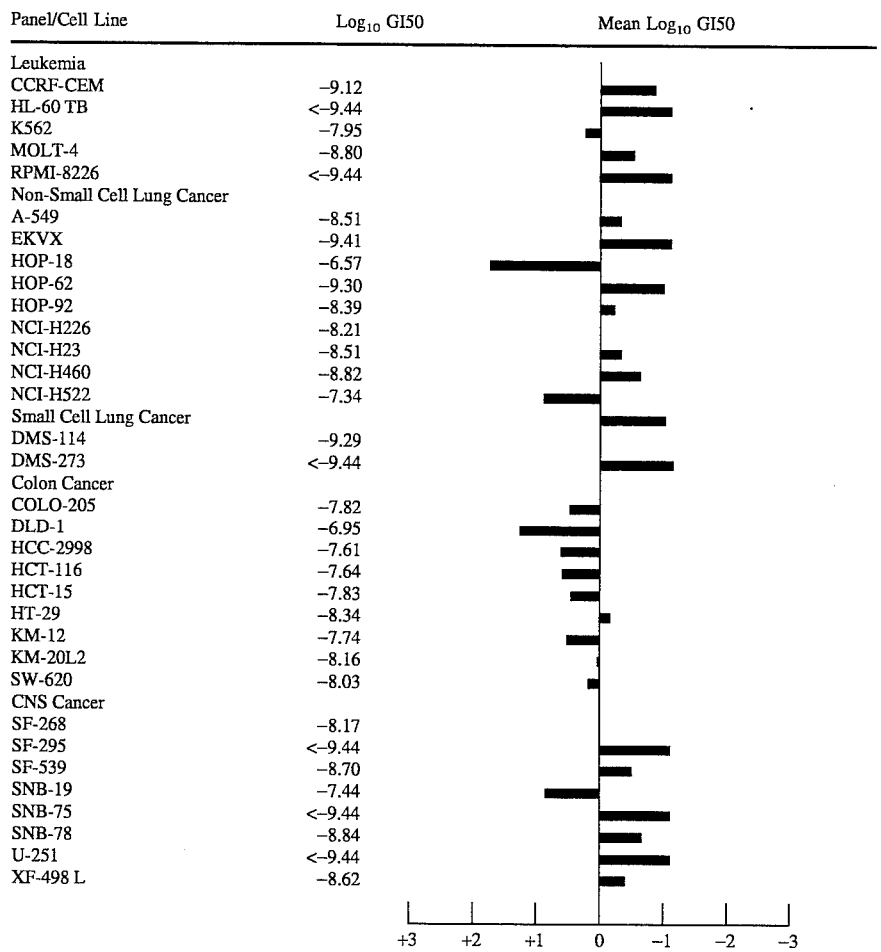

-continued

Example 3
Cephalostatin 9

National Cancer Institute Developmental Therapeutics Program  NSC: 378735-A   Units:
Mean Graphs                                                    Report Date: May 17, 1990

| Panel/Cell Line | $Log_{10}$ GI50 | Mean $Log_{10}$ GI50 |
|---|---|---|
| Melanoma | | |
| LOX-IMVI | −8.16 | |
| MALME-3M | −7.78 | |
| M19-MEL | −6.63 | |
| SK-MEL-2 | −8.11 | |
| SK-MEL-5 | −7.99 | |
| UACC-257 | −7.31 | |
| UACC-62 | −8.42 | |
| Ovarian Cancer | | |
| IGROV-1 | −8.00 | |
| OVCAR-3 | −6.31 | |
| OVCAR-4 | −6.37 | |
| OVCAR-5 | −8.11 | |
| OVCAR-8 | −6.90 | |
| SK-OV-3 | −8.74 | |
| Renal Cancer | | |
| A498 | −8.97 | |
| CAKI-1 | −7.88 | |
| RXF-393 L | <−9.44 | |
| SN-12C | −6.56 | |
| SN12K1 | <−9.44 | |
| UO-31 | −7.59 | |
| Miscellaneous | | |
| MCF-7 | −7.96 | |
| MCF-7/ADR | −6.21 | |
| P388 | <−9.44 | |
| P388/ADR | −7.98 | |
| Mean | −8.20 | |
| Delta | 1.25 | |
| Range | 3.23 | |

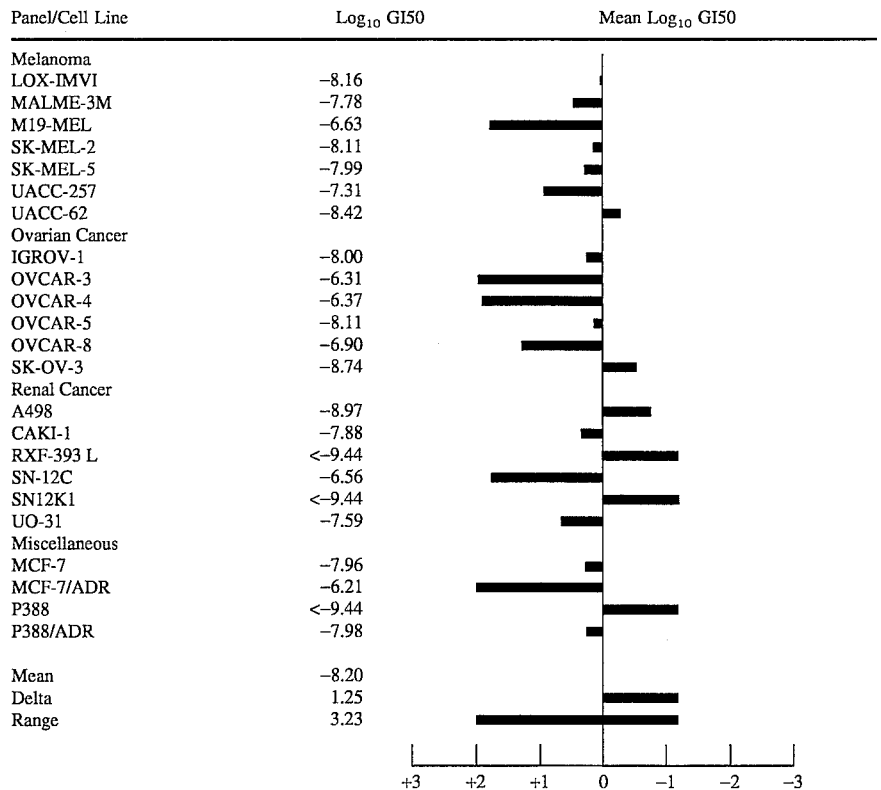

-continued

Example 3
Cephalostatin 9

National Cancer Institute Developmental Therapeutics Program  
Mean Graphs

NSC: 378735-A  Units:  
Report Date: May 17, 1990

| Panel/Cell Line | Log₁₀ GI50 | Mean Log₁₀ GI50 |
|---|---|---|
| Leukemia | | |
| CCRF-CEM | −7.53 | |
| HL-60 TB | −7.24 | |
| K562 | −6.36 | |
| MOLT-4 | −6.42 | |
| RPMI-8226 | −7.35 | |
| Non-Small Cell Lung Cancer | | |
| A-549 | −6.42 | |
| EKVX | −7.32 | |
| HOP-18 | −6.13 | |
| HOP-62 | −8.61 | |
| HOP-92 | −5.95 | |
| NCI-H226 | −6.42 | |
| NCI-H23 | −7.57 | |
| NCI-H460 | −7.44 | |
| NCI-H522 | −6.91 | |
| Small Cell Lung Cancer | | |
| DMS-114 | −7.33 | |
| DMS-273 | −8.76 | |
| Colon Cancer | | |
| COLO-205 | −7.22 | |
| DLD-1 | −5.94 | |
| HCC-2998 | −6.08 | |
| HCT-116 | −6.30 | |
| HCT-15 | −6.48 | |
| HT-29 | −7.32 | |
| KM-12 | −6.24 | |
| KM-20L2 | −6.86 | |
| SW-620 | −7.25 | |
| CNS Cancer | | |
| SF-268 | −6.91 | |
| SF-295 | −9.15 | |
| SF-539 | −7.37 | |
| SNB-19 | −6.48 | |
| SNB-75 | −8.50 | |
| SNB-78 | −6.32 | |
| U-251 | −7.46 | |
| XF-498 L | −7.30 | |

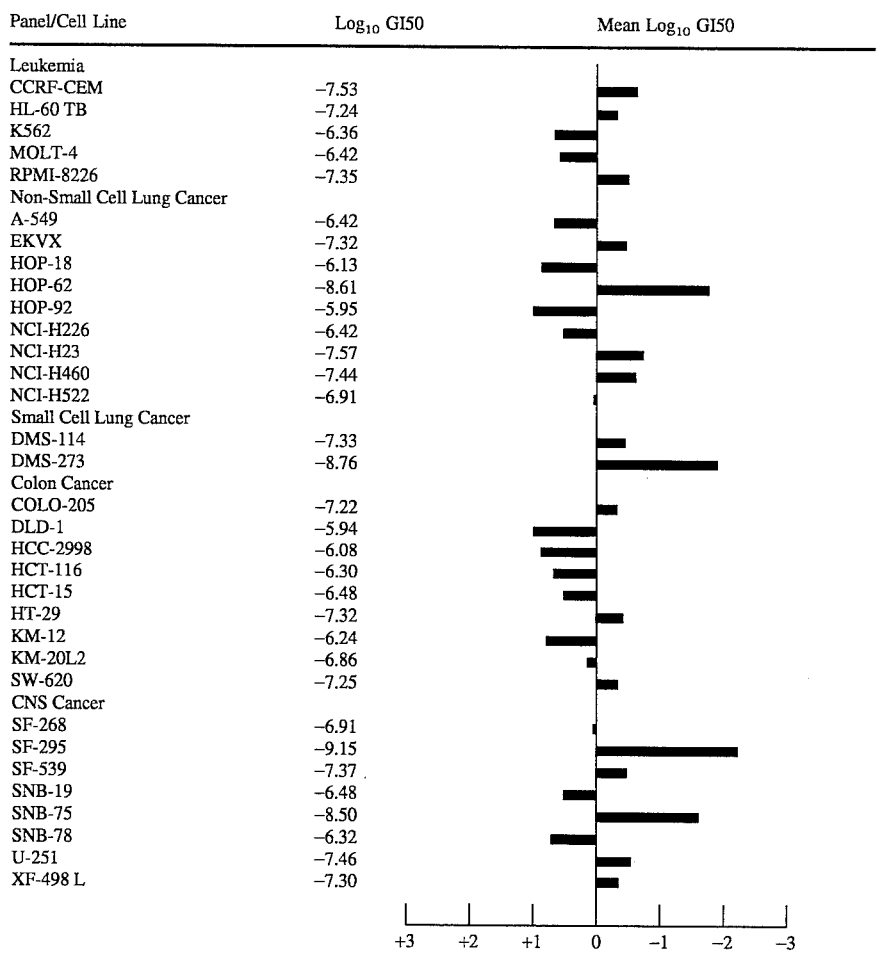

Example 3
Cephalostatin 9

National Cancer Institute Developmental Therapeutics Program  
Mean Graphs

NSC: 378735-A    Units:  
Report Date: May 17, 1990

| Panel/Cell Line | Log$_{10}$ GI50 | Mean Log$_{10}$ GI50 |
|---|---|---|
| Melanoma | | |
| LOX-IMVI | −7.04 | |
| MALME-3M | −7.04 | |
| M19-MEL | −6.14 | |
| SK-MEL-2 | −7.05 | |
| SK-MEL-5 | −7.33 | |
| UACC-257 | −6.95 | |
| UACC-62 | −7.97 | |
| Ovarian Cancer | | |
| IGROV-1 | −6.13 | |
| OVCAR-3 | −5.63 | |
| OVCAR-4 | −5.89 | |
| OVCAR-5 | −7.20 | |
| OVCAR-8 | >−5.44 | |
| SK-OV-3 | −7.55 | |
| Renal Cancer | | |
| A498 | −7.95 | |
| CAKI-1 | −6.38 | |
| RXF-393 L | <−9.44 | |
| SN-12C | −5.54 | |
| SN12K1 | −6.39 | |
| UO-31 | −7.08 | |
| Miscellaneous | | |
| MCF-7 | −6.72 | |
| MCF-7/ADR | −5.56 | |
| P388 | | |
| P388/ADR | −7.05 | |
| Mean | −6.95 | |
| Delta | 2.49 | |
| Range | 4.00 | |

From the foregoing, it is readily apparent that new and useful embodiments of the present invention have been herein described and illustrated which fulfill all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A substantially pure composition of matter selected from the group consisting of cephalostatin 7, cephalostatin 8, and cephalostatin 9.

2. A composition of matter according to claim 1 denominated cephalostatin 7 and having the structure:

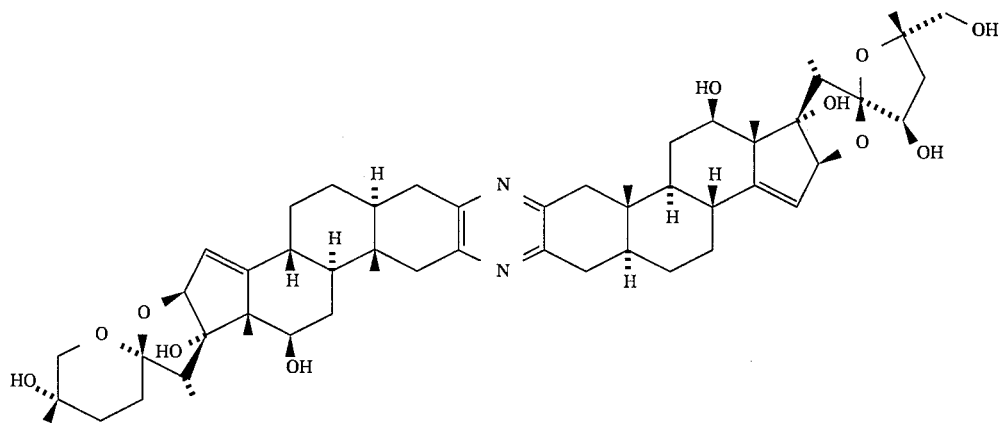

3. A composition of matter according to claim 1 denominated cephalostatin 8 and having the structure:

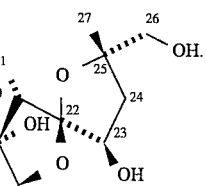
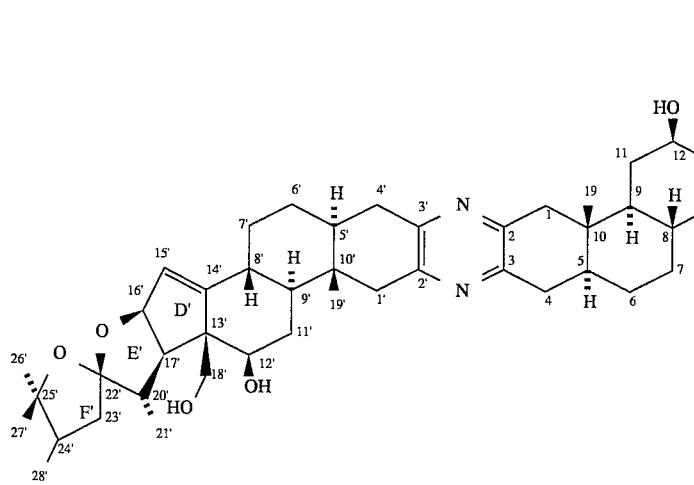
4. A composition of matter according to claim 1 denominated cephalostatin 9 and having the structure:
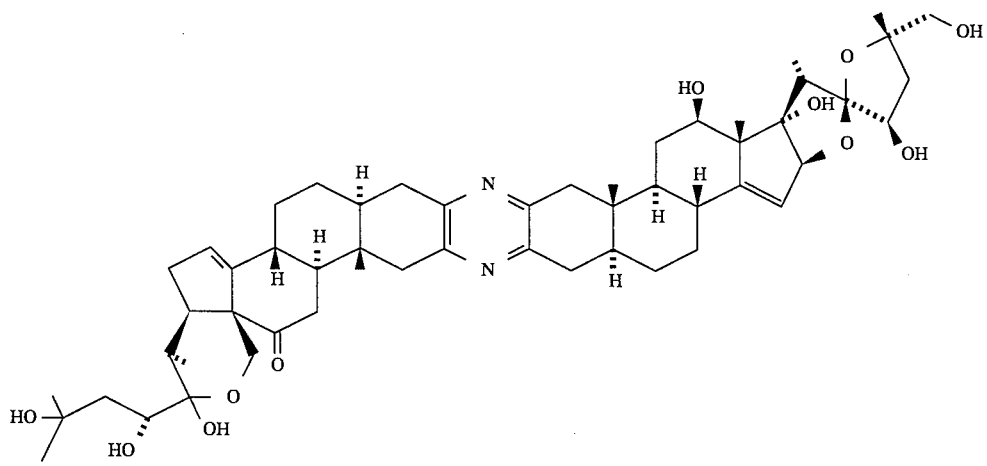
* * * * *